United States Patent
Comaniciu et al.

(10) Patent No.: US 7,555,151 B2
(45) Date of Patent: Jun. 30, 2009

(54) SYSTEM AND METHOD FOR TRACKING ANATOMICAL STRUCTURES IN THREE DIMENSIONAL IMAGES

(75) Inventors: Dorin Comaniciu, Princeton Jct., NJ (US); Bogdan Georgescu, Princeton, NJ (US); Jing Xiao, Sunnyvale, CA (US); Xiang Zhou, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 481 days.

(21) Appl. No.: 11/218,018

(22) Filed: Sep. 1, 2005

(65) Prior Publication Data

US 2006/0064007 A1 Mar. 23, 2006

Related U.S. Application Data

(60) Provisional application No. 60/606,635, filed on Sep. 2, 2004.

(51) Int. Cl.
G06K 9/00 (2006.01)
(52) U.S. Cl. .................. 382/128; 128/922; 600/437
(58) Field of Classification Search ............... 382/128; 128/922; 600/437
See application file for complete search history.

(56) References Cited

U.S. PATENT DOCUMENTS

| | | | | |
|---|---|---|---|---|
| 6,226,418 B1 * | 5/2001 | Miller et al. | ............... | 382/294 |
| 6,301,370 B1 * | 10/2001 | Steffens et al. | ............... | 382/103 |
| 6,491,636 B2 * | 12/2002 | Chenal et al. | ............... | 600/450 |
| 6,537,221 B2 * | 3/2003 | Criton et al. | ............... | 600/454 |
| 6,633,686 B1 * | 10/2003 | Bakircioglu et al. | ........ | 382/294 |
| 6,638,221 B2 * | 10/2003 | Abe et al. | ............... | 600/437 |
| 2005/0228254 A1 * | 10/2005 | Torp et al. | ............... | 600/407 |

FOREIGN PATENT DOCUMENTS

WO 200101859 A 1/2001

OTHER PUBLICATIONS

Georgescu, Bogdan, et al., "Real Time Multi model Tracking of Myocardium in Echocardiography Using Robust Information Fusion," Lecture Notes in Computer Science (2004) vol. 3217, pp. 777-785.

(Continued)

*Primary Examiner*—Brian P Werner
*Assistant Examiner*—Katrina Fujita

(57) ABSTRACT

A system and method for defining and tracking a deformable shape of a candidate anatomical structure wall in a three dimensional (3D) image is disclosed. The shape of the candidate anatomical structure is represented by a plurality of labeled 3D landmark points. At least one 3D landmark point of the deformable shape in an image frame is defined. A 3D cuboid is defined around the detected 3D landmark point. For each landmark point associated with the anatomical structure, its location and location uncertainty matrix is estimated in subsequent frames relative to the reference anatomical structures. A shape model is generated to represent dynamics of the deformable shape in subsequent image frames. The shape model includes statistical information from a training data set of 3D images of representative anatomical structures. The shape model is aligned to the deformable shape of the candidate anatomical structure. The shape model is fused with the deformable shape. A current shape of the candidate anatomical structure is estimated.

26 Claims, 9 Drawing Sheets

OTHER PUBLICATIONS

Zhou X.. S., et al., "Coupled Contour Tracking Through Non orthogonal Projections and Fusion for Echocardiography," Computer Vision (2004) vol. 1, pp. 336-349.

Zhou X.S. et al., "A Unified Framework For Uncertainty Propagation in Automatic Shape Tracking," Computer Vision and Pattern Recognition, (2004) vol. 1 pp. 872-879.

Comaniciu, D. "Institute of Electrical and Electronics Engineers: Nonparametric information fusion for motion estimation" Proceedings 2003 IEEE Conference on Computer Vision and Pattern Recognition, (2003) vol. 2 pp. 59-66.

International Search Report.

* cited by examiner

SYSTEM AND METHOD FOR TRACKING ANATOMICAL STRUCTURES IN THREE DIMENSIONAL IMAGES

CROSS-REFERENCE TO RELATED APPLICATION

This application claims the benefit if U.S. Provisional Application Ser. No. 60/606,635, filed Sep. 2, 2004, which is incorporated by reference in its entirety.

FIELD OF THE INVENTION

The present invention is directed to a system and method for tracking anatomical structures in three dimensional images, and more particularly, to a system and method for tracking motion of anatomical structures in three dimensional images by monitoring trajectories of landmark points associated with the anatomical structure.

BACKGROUND OF THE INVENTION

It is very common during medical examinations for medical imaging systems (e.g., ultrasound imaging systems) to be used for the detection and diagnosis of abnormalities associated with anatomical structures (e.g., organs such as the heart). Many times, the images are evaluated by a medical expert (e.g., a physician or medical technician) who is trained to recognize characteristics in the images which could indicate an abnormality associated with the anatomical structure or a healthy anatomical structure.

Because of the advancements in computer technology, most computers can easily process large amounts of data and perform extensive computations that can enhance the quality of the obtained images. Furthermore, image processing can be used as a tool to assist in the analysis of the images. Efficient detection of anatomical structures or objects of interest in an image is an important tool in the further analysis of that structure. Many times abnormalities in the shape of an anatomical structure or changes of such a shape through time (e.g., a beating heart or a breathing lung) indicate a tumor or various diseases (e.g., dilation or ischemia of the heart muscle).

This type of image processing can be used for other applications such as the detection of human faces in an image. Because of the variables associated with different facial features (e.g., hair color and length, eye color, facial shape, etc.), facial detection is not a trivial task. Face detection can be used in a variety of applications such as user recognition, surveillance or security applications.

Various types of approaches have been used to detect objects of interest (e.g., anatomical structures or faces). Component-based object detectors (eye detector and mouth detector, etc.) can deal with large variations in pose and illumination, and are more robust under occlusions and heteroscedastic noise. For example, in echocardiogram analysis, local appearance of the same anatomical structure (e.g., the septum) is similar across patients, while the configuration or shape of the heart can be dramatically different due to, for example, viewing angles or disease conditions. Likewise, in face detection, general spatial relationships between facial features are fairly consistent (e.g., general location of eyes to nose and mouth), while the configuration and shape of the various facial features (e.g., shape of eyes, expression of mouth, and relative distances among them) can vary significantly.

For most visual tracking applications, measurement data are uncertain and sometimes missing: images are taken with noise and distortion, while occlusions can render part of the object-of-interest unobservable. Uncertainty can be globally uniform; but in most real-world scenarios, it is heteroscedastic in nature, i.e., both anisotropic and inhomogeneous. A good example is the echocardiogram (ultrasound heart data). Ultrasound is prone to reflection artifacts, e.g., specular reflectors, such as those that come from membranes. Because of the single "view direction", the perpendicular surface of a specular structure produces strong echoes, but tilted or "off-axis" surfaces may produce weak echoes, or no echoes at all (acoustic "drop out"). For an echocardiogram, the drop-out can occur at the area of the heart where the tissue surface is parallel to the ultrasound beam.

Due to its availability, relative low cost, and noninvasiveness, cardiac ultrasound images are widely used for assessing cardiac functions. In particular, the analysis of ventricle motion is an efficient way to evaluate the degree of ischemia and infarction. Segmentation or detection of the endocardium wall is the first step towards quantification of elasticity and contractility of the left ventricle. Examples of some existing methods include pixel-based segmentation/clustering approaches (e.g., Color Kinesis), variants of optical flow, deformable templates and Markov random process/fields, and active contours/snakes. The methods are employed in 2-Dimensional, 3-Dimensional or 4-Dimensional (3D+time) space.

However, most existing segmentation or detection methods do not attempt to recover accurate regional motions of the endocardial wall, and in most cases, motion components along the wall are ignored. This simplified treatment is also employed by contour trackers that search only along the normals of the current contour. This is not suitable for regional wall abnormality detection, because regional motion of an abnormal left ventricle is likely to be off the normal of the contour, not to mention that global motion, such as translation or rotation (due to the sonographer's hand motion or respiratory motion the patient), causes off-normal local motion on the contour as well. It is desirable to track the global shape of endocardial wall as well as its local motion, for the detection of regional wall motion abnormalities. This information can be used for further diagnosis of ischemia and infarction. Furthermore with the recent introduction of three dimensional ultrasound images, even more detail relating to the endocardial wall can be obtained. There is a need for a framework that tracks three dimensional motion of anatomical structures.

SUMMARY OF THE INVENTION

A system and method for defining and tracking a deformable shape of a candidate anatomical structure wall in a three dimensional (3D) image is disclosed. The shape of the candidate anatomical structure is represented by a plurality of labeled 3D landmark points. At least one 3D landmark point of the deformable shape in an image frame is defined. A 3D cuboid is defined around the detected 3D landmark point. For each landmark point associated with the anatomical structure, its location and location uncertainty matrix is estimated in subsequent frames relative to the reference anatomical structures. A shape model is generated to represent dynamics of the deformable shape in subsequent image frames. The shape model includes statistical information from a training data set of 3D images of representative anatomical structures. The shape model is aligned to the deformable shape of the candidate anatomical structure. The shape model is fused with the deformable shape. A current shape of the candidate anatomical structure is estimated.

BRIEF DESCRIPTION OF THE DRAWINGS

Preferred embodiments of the present invention will be described below in more detail, wherein like reference numerals indicate like elements, with reference to the accompanying drawings.

DETAILED DESCRIPTION

The present invention is directed to a system and method for tracking three dimensional motion of an anatomical structure. An example where such a method would be utilized is for detecting regional wall motion abnormalities in the heart by diction and segmentation of the ventricle endocardial or epicardial borders through machine learning, or classification, and by identifying similar cases from annotated databases. It is to be understood by those skilled in the art that the present invention may be used in other applications where motion tracking is useful such as, but not limited to, surveillance. The present invention can also be used in 4 dimensional (3D+ time) data analysis, such as medical analysis of anatomical structures such as the heart, lungs or tumors, which can be evolving over time.

Figure 1:
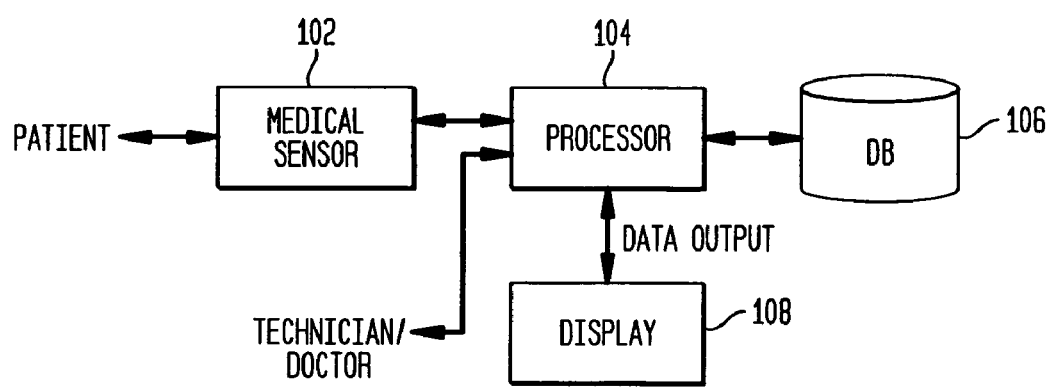
FIG. 1 illustrates an exemplary architecture of an echocardiograph system that uses a method for tracking three dimensional motion of an endocardial wall of a left ventricle in accordance with the present invention.

For purposes of describing the present invention, an example will be described for detecting the endocardial wall of the left ventricle of a human heart. FIG. 1 illustrates an exemplary architecture of an echocardiograph system that uses a method for tracking three dimensional (3D) motion of an endocardial wall of a left ventricle in accordance with the present invention. A medical sensor 102, such as an ultrasound transducer is used to perform an examination on a patient. The sensor 102 is used to obtain medical measurements consistent with a particular medical examination. For example, a patient experiencing heart problems may have an echocardiogram performed to help diagnose the particular heart ailment. An ultrasound system provides two-, three-, and four (3D+time)-dimensional images of the heart from various perspectives. In accordance with the present invention, 3D images of the heart are obtained.

The information obtained by the sensor 102 is communicated to a processor 104 which may be a workstation or personal computer. The processor 104 converts the sensor data into an image that is communicated to display 108. The display 108 may also communicate other graphical information or tables of information relating to the image. In accordance with the present invention, the processor 104 is also provided with data representing landmark points that are associated with the endocardial wall as will be described in further detail hereinafter. The data may be provided manually by a user such as a physician or sonographer, or automatically by the processor 104. The landmark points comprise a series of individual points, the movement of which is tracked by the processor 104 and illustrated on display 108.

In addition to data from the medical sensor 102, the processor 104 may also receive other data inputs. For example, the processor may receive data from a database 106 associated with the processor 104. Such data may include subspace models that represent potential contour shapes for the endocardial wall. These subspace models may be images of left ventricles that are representative of a plurality of patients or may be computer generated models of contour shapes based on statistical information. The processor 104 tracks the individual points of the contour shape using known approaches such as Bayesian kernel matching or optical flow-based methods. Error accumulation during tracking is remedied by using a multi-template adaptive matching framework. Uncertainty of tracking is represented at each point in the form of a covariance matrix, which is subsequently fully exploited by a subspace shape constraint using a non-orthogonal projection.

Figure 2:
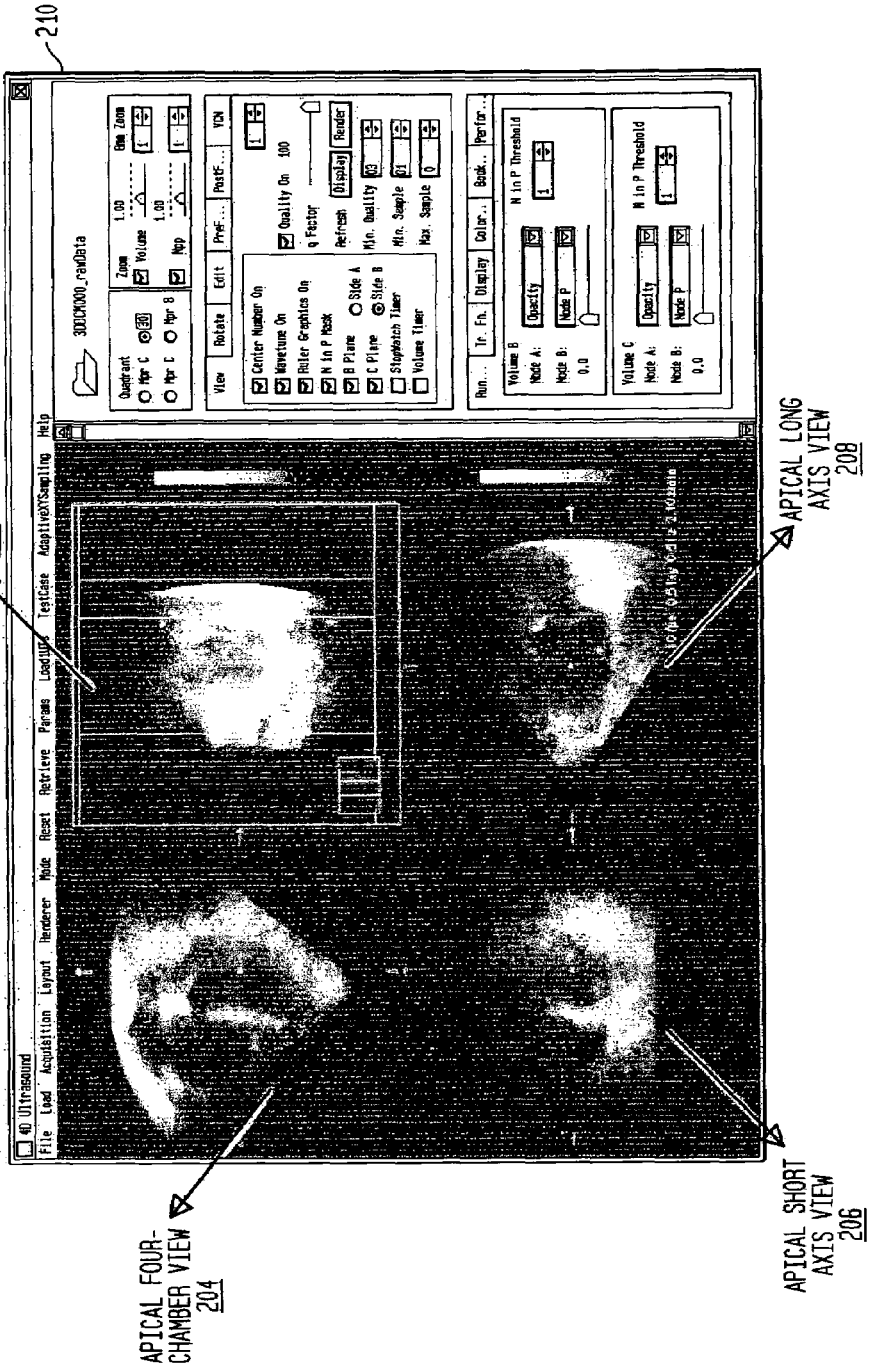
FIG. 2 illustrates an exemplary screen shot of a view of a three dimensional ultrasound image of a heart in accordance with the present invention.

FIG. 2 illustrates an exemplary screen shot of a 3D ultrasound image 202 of a heart in accordance with the present invention. In addition to the 3D image 202, there are also shown slices from three orthogonal views. Orthogonal view 204 illustrates an apical four chamber view of the heart. Orthogonal view 206 illustrates an apical short axis view of the heart and orthogonal view 208 illustrates an apical long axis view of the heart. In addition, a user interface 210 is shown which allows a user to modify the images by for example adding rulers to the image or by adjusting the resolution of the image. In the initialization stage of the method of the present invention, a number of landmark points on the Left Ventricle (LV) wall are specified. The pose of these landmark points are individually tracked across a time sequence of images. The trajectories of all the landmark points are then used to analyze the 3D motion and deformation of the LV wall. In accordance with the present invention, the landmark points are distributed evenly on the interior LV wall surface and refer to the meaningful heart segments defined in standard echocardiography standards.

Figure 3:
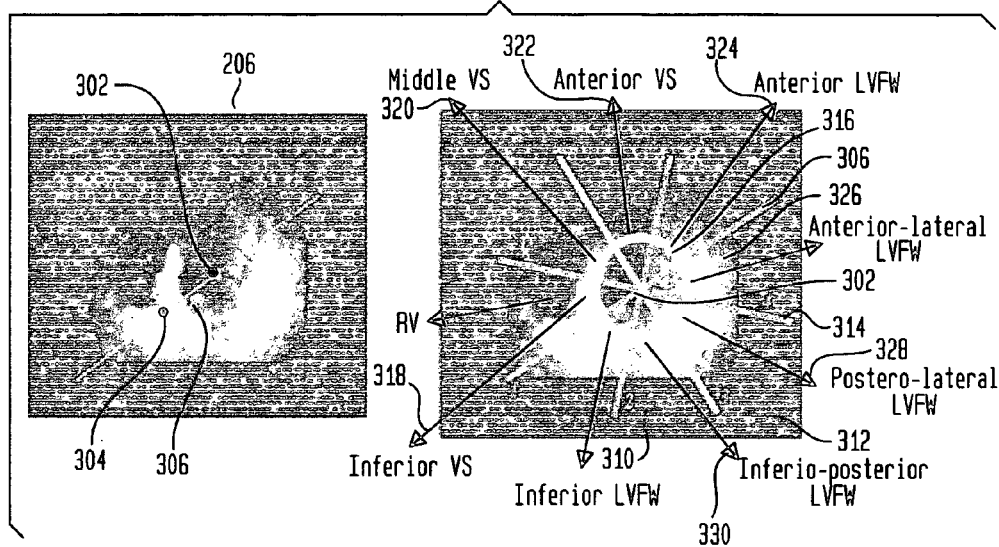
FIG. 3 illustrates a short axis view of a left ventricle and its segmentation in accordance with the present invention.

The following describes an exemplary method for defining the landmark points in accordance with the present invention. The short axis view slice 206 of the mid-ventricular region is used to specify the heart segments along the short axis view. FIG. 3 illustrates how the short axis view segments are labeled in accordance with the present invention. A point 302 identifies the center of the LV and an intersecting point 304 of the inferior Right Ventricle (RV) and the inferior Ventricular Septum (VS) is specified. A line 306 connects the points 302,304 that separate the inferior VS segment from the inferior Left Ventricle Free Wall (LVFW) and the anterior LVFW from the antero-lateral LVFW. The other three lines 310, 312, 314 are determined automatically by rotating the first line in 45 degrees increments with respect to the LV center 302. The LVFW and VS are then divided into eight segments 318 330 by the four lines 306, 310, 312, 314. Each of the lines 306, 310, 312, 314 represents a 3D slice along the short axis view and the circle 316 represents the location of the myocardium of the left ventricle.

Figure 4:
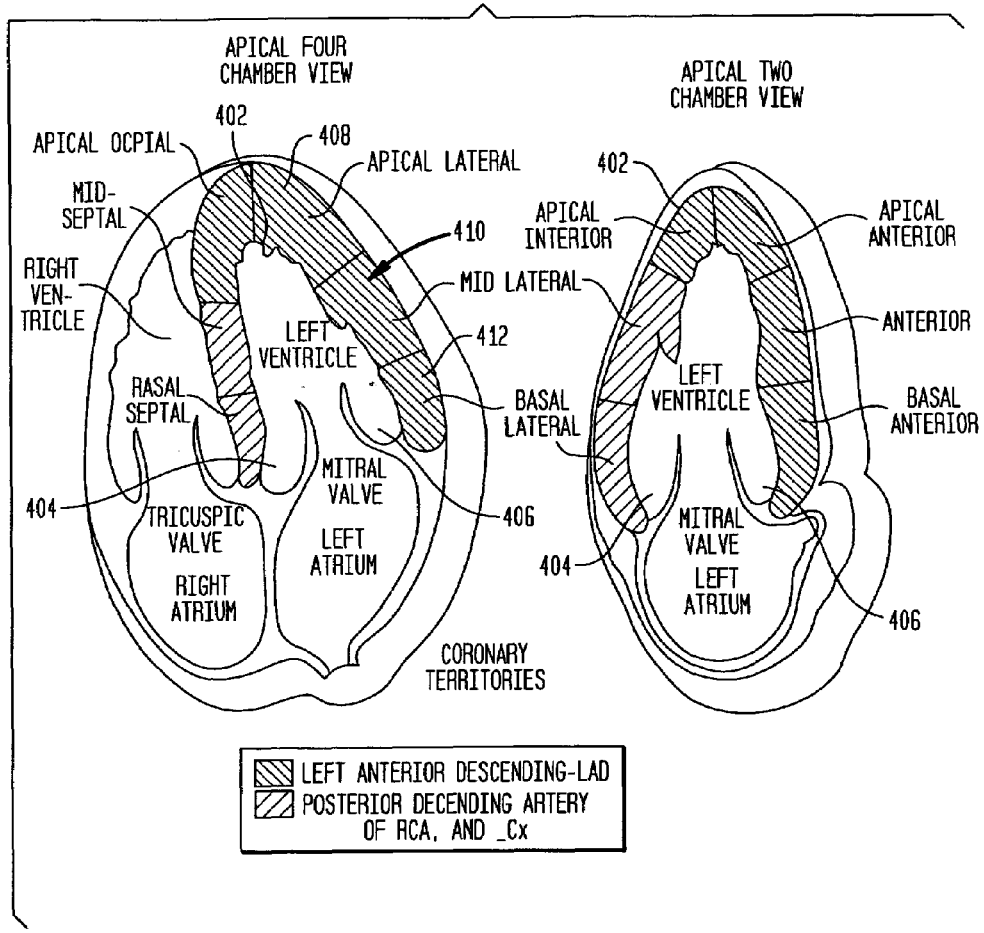
FIG. 4 illustrates LV wall segments that are perpendicular to the short axis view of FIG. 3.
Figure 5:
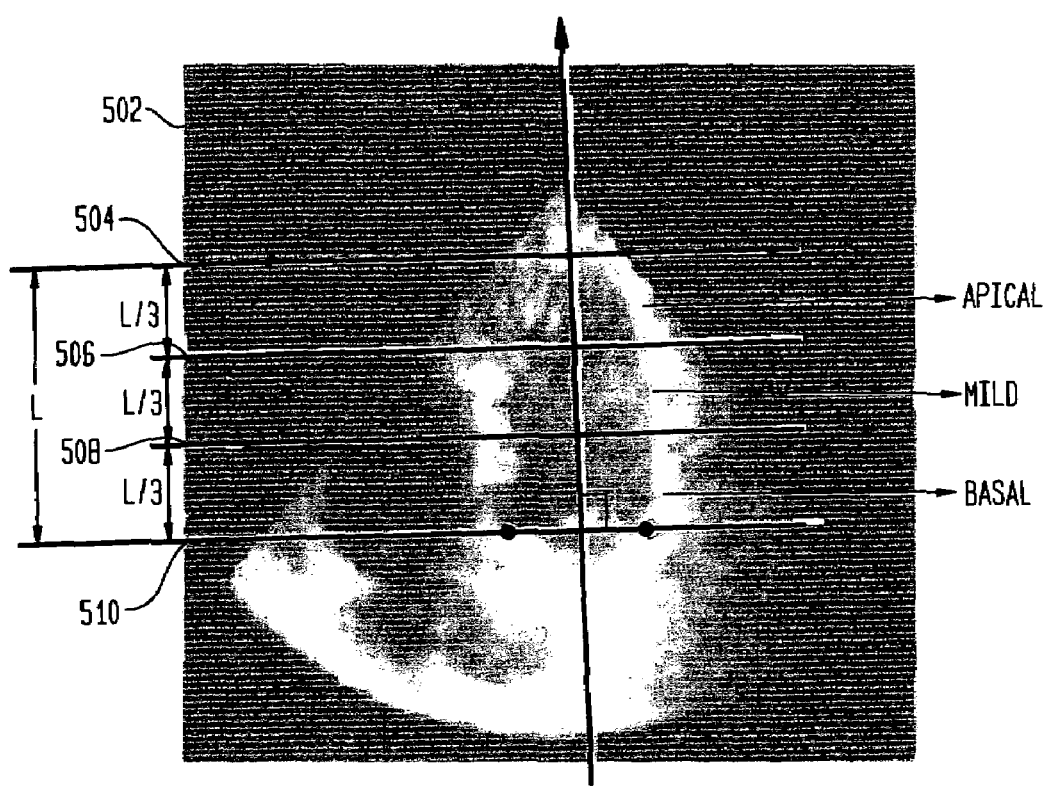
FIG. 5 illustrates the image of the short axis view of the LV of FIG. 3 in which the perpendicular segments are labeled in accordance with the present invention.

FIG. 4 illustrates the heart segments that are perpendicular to the short axis view defined in FIG. 3. From the four slices 306, 310, 312, 314, the slice 314 between the antero-lateral LVFW and the postero-lateral LVFW is extracted as the four chamber view. The LV apex 402 and the two bottom corner points 404, 406 of the LV wall are first specified. Between the apex 402 and the bottom 404, 406, the LV wall is segmented into three parts, apical 408, mid 410 and basal 412, each with equal heights. The LV wall is not necessarily captured in a straight pose. Its pose in the 3D ultrasound image might be tilted. To achieve good initialization, the 3D pose of the LV wall needs to be adjusted. The pose, i.e., the orientation of the segmenting slices, along the four-chamber view is determined by a line 502 connecting the apex and the center of the two bottom points as shown in FIG. 5. Then four segmenting slices 504, 506, 508, 510 along the four chamber view (vertical) are determined as the slices perpendicular to the orientation line and with equal distances L/3 between the apex and bottom.

Figure 6:
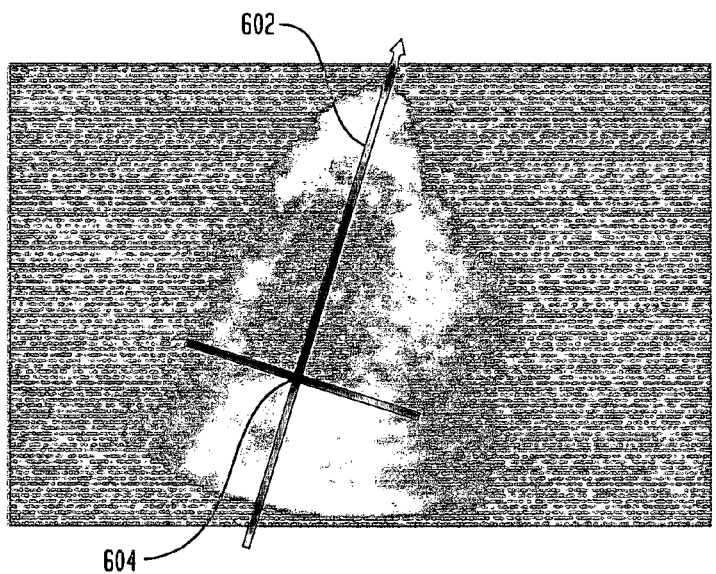
FIG. 6 illustrates the image of the long axis view of the LV of FIG. 3 in accordance with the present invention.

When dealing with a 3D object, the LV pose along the long-axis view also needs to be determined. After adjusting the poses of the four segmenting slices along the four chamber view, the slice (slice 310 in FIG. 3) between the inferior LVFW and the infero-posterior LVFW is extracted as the long axis view as shown in FIG. 6. The center point 604 at the bottom has been determined in the previous processes. The LV apex 602 is specified in this image and then the LV pose along the long-axis view is determined.

Figure 7:
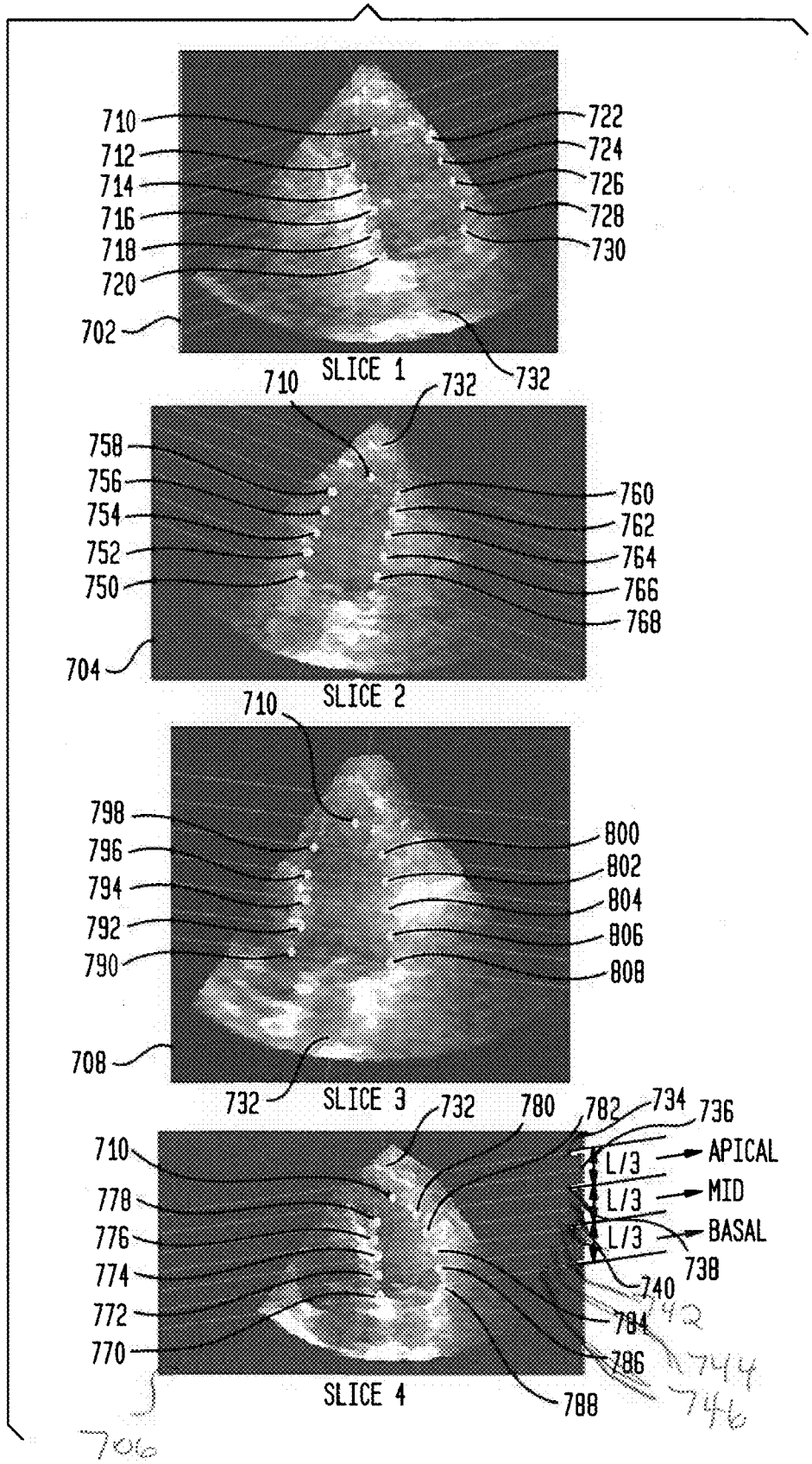
FIG. 7 illustrates images of the slices made to the short axis view of the LV in FIG. 3 and landmark points in accordance with the present invention.

The four horizontal segmenting slices and four vertical segmenting slices have been determined and their poses adjusted according to the LV pose. The four segmenting slices 702, 704, 706, 708 perpendicular to the short axis view have been extracted. For each slice, one point 710 is specified at the apex and ten points 712-730, 750-768, 770-788 and 790-808 evenly distributed along the interior surface o the LV wall and VS as illustrated in FIG. 7. Note that the intersecting line 732 of the four slices 702-708 helps to localize the apex point and the segmenting slices 734-746 parallel to the short axis view constrain the landmarks to be evenly distributed. The coordinates of the four apex landmarks 710 are averaged to achieve the final apex location. Thus 41 landmark points are obtained which represent all the LV wall segments. During the entire initialization step, 50 points need to be specified.

Figure 8:
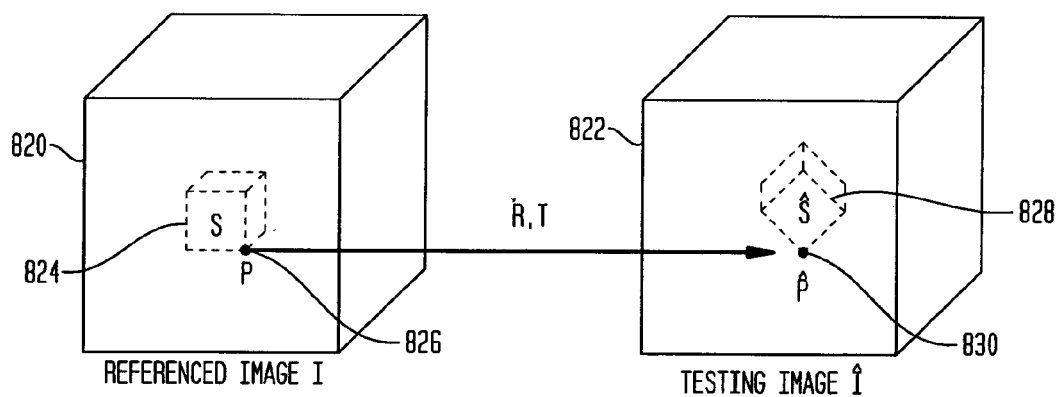
FIG. 8 illustrates 3D motion of a 3D point in accordance with the present invention.

Given a 3D point 826 in reference image I 820, the displacement of its 3D location is recovered in the testing image Î 822 as shown in FIG. 8. Since the constraints from a single point are not sufficient to estimate its 3D motion, the points in a 3D cuboid 824 surrounding that point 826 are assumed to share the same motion and use the same constraints from all the points to recover the motion parameters. The full 3D motion includes both rotation R and translation T. But in some cases, it can be simplified to be pure translation. As can be seen in testing image Î 822, by tracking the motion of the 3D cuboid Ŝ 828 the new location of the single point P̂ 830 can be determined.

The present invention includes approaches to recovering the motion parameters for both rotation and translation. In these approaches the following assumptions are made:

The 3D cuboid is locally rigid, i.e.

$$\hat{P} = \begin{pmatrix} \hat{x} \\ \hat{y} \\ \hat{z} \end{pmatrix} = RP + T = R \begin{pmatrix} x \\ y \\ z \end{pmatrix} + \begin{pmatrix} t_x \\ t_y \\ t_x \end{pmatrix} \quad (1)$$

The intensity of the same point is invariant in different images, i.e.

$$\hat{I}(\hat{P}) = I(P) \quad (2)$$

The motion between neighboring frames is instantaneous, i.e.

$$R \approx \begin{pmatrix} 1 & -\theta_z & \theta_y \\ \theta_z & 1 & -\theta_x \\ -\theta_y & \theta_x & 1 \end{pmatrix} \quad (3)$$

For all the 3D points in the cuboid S, the following objective function is minimized to estimate the motion parameters.

$$\min E = \sum_{P \in S} \left( \hat{I}(\hat{P}) - I(P) \right)^2 \quad (4)$$

Based on the above assumptions, $$\hat{P} = \begin{pmatrix} \hat{x} \\ \hat{y} \\ \hat{z} \end{pmatrix} = \begin{pmatrix} x \\ y \\ z \end{pmatrix} + \begin{pmatrix} 0 & -\theta_z & \theta_y \\ \theta_z & 0 & -\theta_x \\ -\theta_y & \theta_x & 0 \end{pmatrix} \begin{pmatrix} x \\ y \\ z \end{pmatrix} + \begin{pmatrix} t_x \\ t_y \\ t_x \end{pmatrix} = \quad (5)$$

$$\begin{pmatrix} x \\ y \\ z \end{pmatrix} + \begin{pmatrix} z\theta_y - y\theta_z + t_x \\ x\theta_z - z\theta_x + t_y \\ y\theta_x - x\theta_y + t_z \end{pmatrix}$$

$$\hat{I}(\hat{P}) = \hat{I} \left( P + \begin{pmatrix} z\theta_y - y\theta_z + t_x \\ x\theta_z - z\theta_x + t_y \\ y\theta_x - x\theta_y + t_z \end{pmatrix} \right) \quad (6)$$

Performing the first order Taylor Expansion, results in $$\hat{I}(\hat{P}) \approx \hat{I}(P) + \quad (7)$$

$$\underbrace{(y\hat{I}_z - z\hat{I}_y \quad z\hat{I}_x - x\hat{I}_z \quad x\hat{I}_y - y\hat{I}_x \quad \hat{I}_x \quad \hat{I}_y \quad \hat{I}_z)}_{\text{Jacobian matrix } J} \underbrace{\begin{pmatrix} \theta_x \\ \theta_y \\ \theta_z \\ t_x \\ t_y \\ t_z \end{pmatrix}}_{\text{Motion parameters: } \Delta\mu}$$

Then,

-continued $$E = \sum_{P \in S} \left( \frac{\hat{I}(P) - I(P)}{I_{tp}} + J_P \cdot \Delta\mu \right)^2 \quad (8)$$

Therefore, $$\Delta\mu = -\underbrace{\left( \sum_{P \in S} J_P^T J_P \right)^{-1}}_{\text{Hessian matrix } H} \left( \sum_{P \in S} I_{tP} J_P^T \right) \quad (9)$$

Figure 9:
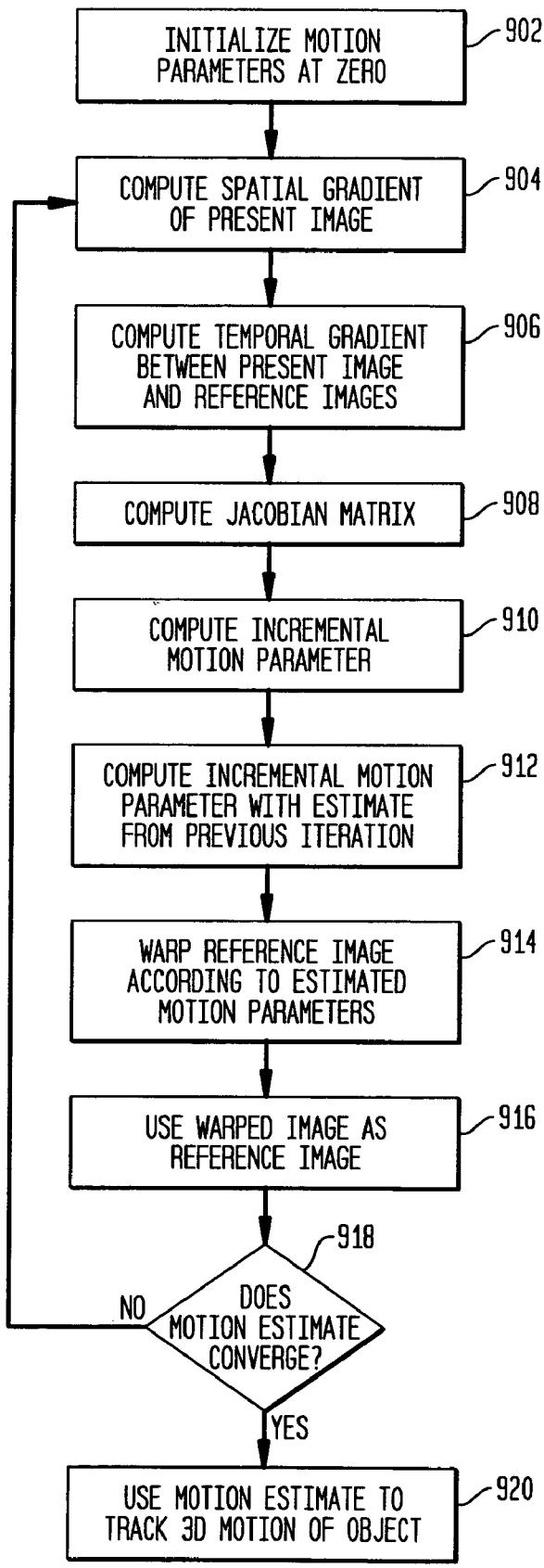
FIG. 9 is a flow chart that outlines a method for estimating 3D motion of an anatomical structure in accordance with the present invention.

In accordance with the present invention, FIG. 9 outlines a method for estimating the 3D motion of an anatomical structure. As part of the initialization, the motion parameters are set to zero (step 902). Next the spatial gradient of the present image is computed (step 904). In addition, the temporal gradient between the present and reference images is computed (step 906) and the Jacobian matrix is computed (step 908). The incremental motion parameter is next computed using Equation (9) (step 910). The incremental motion parameter is also computed using an estimate from the previous iteration (step 912).

The reference image is warped according to the estimated motion parameters (step 914). The warped image is now used as the reference image (step 916) and the method returns to step 904. Steps 904-916 are repeated until the motion estimate converges (step 918). When the motion estimates converge, the motion estimate is used to track the 3D motion of the anatomical structure (step 920).

Figure 10:
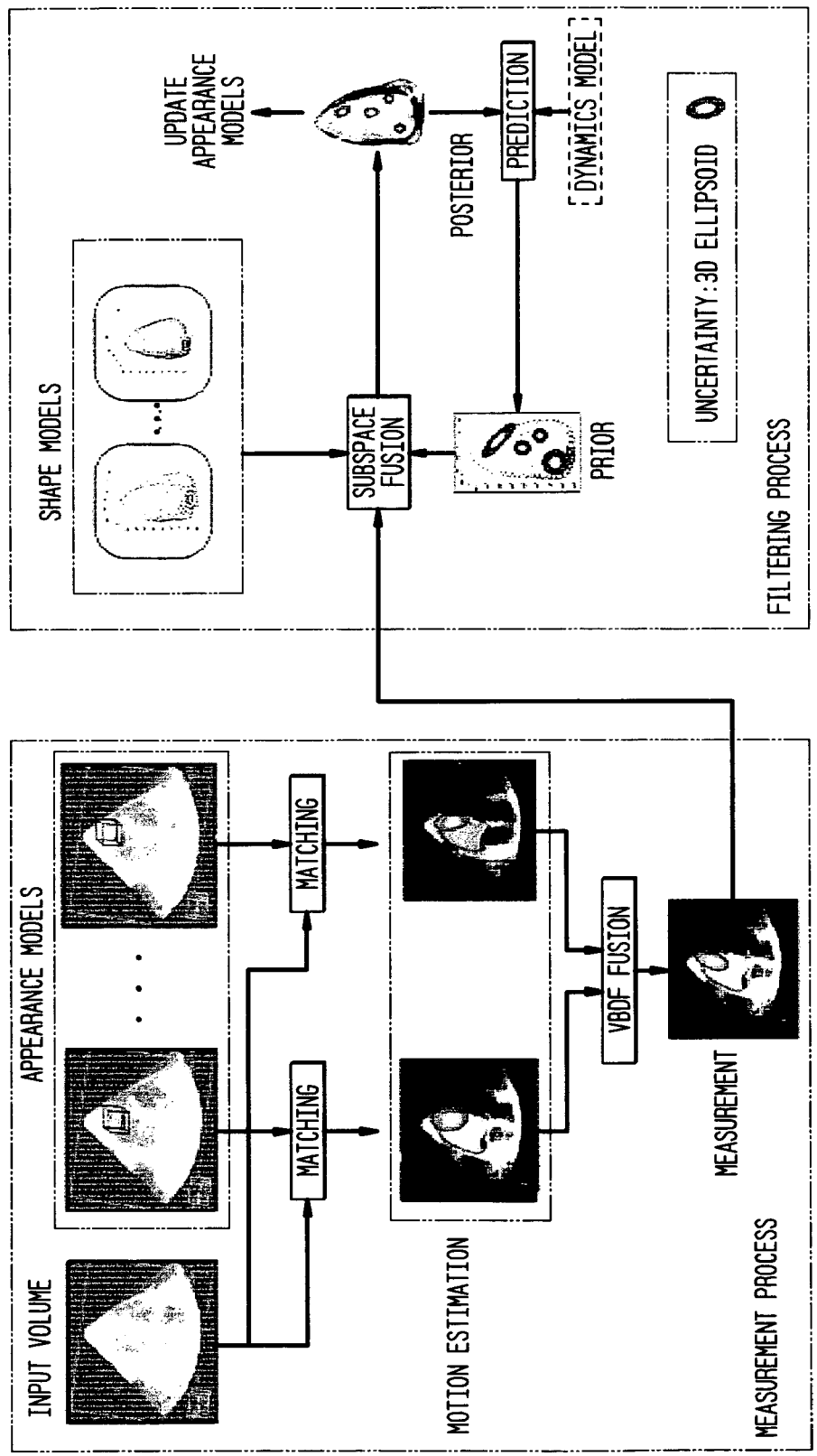
FIG. 10 illustrates uncertainty propagation during shape detection and tracking in accordance with the present invention.

FIG. 10 shows a schematic diagram of the analysis steps where the uncertainty of detection is propagated through all the steps. At each frame, multiple detection candidates are evaluated by comparing their likelihood in the context of both the shape model, and the prediction from the previous frame based on the system dynamics. Ellipses illustrate the location uncertainties. Uncertainties are transformed with the shape during alignment and fused with the model and the predicted prior information during likelihood estimation and tracking.

Having described embodiments for a method for estimating 3D motion of an anatomical structure, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

We claim:

1. A method for tracking 3-dimensional (3D) motion of a deformable shape of a candidate anatomical structure across a sequence of three dimensional (3D) images the method comprising the steps of:
   specifying a plurality of landmark points on a deformable shape of a candidate anatomical structure in a present 3D image of said structure, wherein the landmark points are distributed evenly on said deformable shape;
   defining a 3D cuboid around at least one 3D landmark point;
   computing a Jacobian matrix from a temporal gradient between the present image and a reference images;
   computing motion parameters from said Jacobian matrix and present and reference image values in said cuboid;
   warping the cuboid in the reference image according to the motion parameters, and redefining the warped image to be the reference image;
   repeating said steps of computing a temporal gradient and a Jacobian matrix, computing motion parameters, and warping the reference image until convergence; and
   using the motion parameters to track 3D motion of the anatomical structure.

2. The method of claim 1 wherein localization uncertainties of the plurality of 3D landmark points are represented by covariance matrices.

3. The method of claim 1, further comprising the steps of:
   matching the 3D landmark points of the candidate anatomical structure to corresponding landmark points of a reference anatomical structure.

4. The method of claim 3, further comprising the step of:
   transforming an orientation of the candidate anatomical structure to a same orientation of the reference anatomical structure.

5. The method of claim 4 wherein the transformation includes translation of the image of the candidate anatomical structure.

6. The method of claim 4 wherein the transformation includes rotation of the image of the candidate anatomical structure.

7. The method of claim 4 wherein the transformation includes scaling of the image of the candidate anatomical structure.

8. The method of claim 1 wherein the anatomical structure is a left ventricle.

9. The method of claim 8, wherein specifying a plurality of landmark points on said deformable shape comprises:
   identifying a center point of the LV in a short axis view slice of the mid-ventricular region;
   specifying an intersecting point of the inferior right ventricle (RV) and the inferior ventricular septum (VS) in the short axis view slice;
   connecting the center point and the intersecting point with a first line that separates the inferior VS from the inferior left ventricle free wall (LVFW) and the anterior LVFW from the antero-lateral LVFW;
   determining second, third and fourth lines by rotating said first line in 45 degrees increments with respect to the LV center point;
   dividing the LVFW and VS into eight segments by the first, second third and fourth lines wherein each of the first, second third and fourth lines represents a 3D slice along the short axis view;
   extracting a slice between an antero-lateral LVFW and a postero-lateral LVFW as a four chamber view;
   specifying an LV apex and first and second bottom corner points of an LV wall;
   segmenting the LV wall into an apical part, a mid part, and a basal part between said apex and said first and second bottom points, each LV wall part having substantially equal height;
   adjusting a 3D pose of the LV wall;
   determining the LV pose along a long-axis view;
   for each 3D slice along the short axis view, specifying one point at the apex and ten points evenly distributed along an interior surface of the LV wall and VS; and
   averaging the coordinates of the apex points to determine a final apex location.

10. The method of claim 9, wherein adjusting a 3D pose of the LV wall comprises:
  defining an orientation line connecting the apex point and a center point between the first and second bottom points; and
  defining first, second, third, and fourth segmenting slices along the four chamber view as slices substantially perpendicular to the orientation line with substantially equal distances between the apex and a bottom line connecting the first and second bottom corner points.

11. The method of claim 9, wherein determining the LV pose along a long-axis view comprises:
  extracting a slice between an inferior LVFW and an infero-posterior LVFW as a long axis view; and
  specifying the LV apex in said long axis view and determining the LV pose along the long-axis view based on the LV apex and the LV center point.

12. The method of claim 1 wherein the image is a 3D ultrasound image.

13. The method of claim 1, wherein computing motion parameters includes using estimated motion parameters from a previous iteration.

14. The method of claim 1, wherein computing motion parameters from said Jacobian matrix and present and reference image values in said cuboid comprises calculating $$\Delta\mu = -\left(\sum_{P\in S} J_P^T J_P\right)^{-1} \left(\sum_{P\in S} I_{tP} J_P^T\right),$$

wherein $\Delta\mu=(\theta_x,\theta_y,\theta_z,t_x,t_y,t_z)$ wherein $\theta_i$ is an infinitesimal rotation in the ith direction $t_i$ a translation in the ith direction, $I_{tP}=\hat{I}(\hat{P})-I(P)$ wherein I is the reference image and P is the at least one point in the reference image, $\hat{I}$ is the present image and $\hat{P}$ is the point $\hat{I}$ corresponding to P. $J_p$ is the Jacobian matrix, and S is the cuboid.

15. A method for tracking 3-dimensional (3D) motion of a left ventricle (LV) all across a sequence of three dimensional (3D) images of a heart, said method comprising the steps of:
  identifying a center point of the LV in a short axis view slice of the mid-ventricular region;
  specifying an intersecting point of the inferior right ventricle (RV) and the inferior ventricular septum (VS) in the short axis view slice;
  connecting the center point and the intersecting point with a first line that separates the inferior VS from the inferior left ventricle free wall (LVFW) and the anterior LVFW from the antero-lateral LVFW;
  determining second, third and fourth lines by rotating said first line in 45 degrees increments with respect to the LV center point;
  dividing the LVFW and VS into eight segments by the first, second third and fourth lines, wherein each of the first, second third and fourth lines represents a 3D slice along the short axis view;
  extracting a slice between an antero-lateral LVFW and a postero-lateral LVFW as a four chamber view;
  specifying an LV apex and first and second bottom corner points of an LV wall;
  segmenting the LV wall into an apical part, a mid part, and a basal part between said apex and said first and second bottom points, each LV wall part having substantially equal height;
  adjusting a 3D pose of the LV wall;
  determining the LV pose along a long-axis view;
  for each 3D slice along the sho axis view specifying as landmark points one point a the apex and ten points evenly distributed along an interior surface of the LV wall and VS;
  averaging the coordinates of the apex points to determine a final landmark point;
  individually tracking the pose of the landmark points across a time sequence of images; and
  using trajectories of the landmark points to analyze 3D motion and deformation of the LV wall.

16. The method of claim 15, wherein tracking the pose of a landmark point comprises:
  defining a 3D cuboid around at least one 3D landmark point;
  computing a Jacobian matrix from a temporal gradient between the present image and a reference images;
  computing motion parameters from said Jacobian matrix and present and reference image values in said cuboid;
  warping the cuboid in the reference image according to the motion parameters, and redefining the warped image to be the reference image; and
  repeating said steps of computing a temporal gradient and a Jacobian matrix, computing motion parameters, and warping the reference image until convergence.

17. A program storage device readable by a computer, tangibly embodying a program of instructions executable by the computer to perform the method steps for tracking 3-dimensional (3D) motion of a deformable shape of a candidate anatomical structure across a sequence of three dimensional (3D) images, the method comprising the steps of:
  specifying a plurality of landmark points on a deformable shape of a candidate anatomical structure in a present 3D image of said structure, wherein the landmark points are distributed evenly on said deformable shape;
  defining a 3D cuboid around at least one 3D landmark point;
  computing a Jacobian matrix from a temporal gradient between the present image and a reference images;
  computing motion parameters from said Jacobian matrix and present and reference image values in said cuboid;
  warping the cuboid in the reference image according to the motion parameters, and redefining the warped image to be the reference image
  repeating said steps of computing a temporal gradient and a Jacobian matrix, computing motion parameters, and warping the reference image until convergence; and
  using the motion parameters to track 3D motion of the anatomical structure.

18. The computer readable program storage device of claim 17, the method further comprising:
  matching the 3D landmark points of the candidate anatomical structure to corresponding landmark points of a reference anatomical structure.

19. The computer readable program storage device of claim 17, the method further comprising:
  transforming an orientation of the candidate anatomical structure to a same orientation of the reference anatomical structure.

20. The computer readable program storage device of claim 17, wherein the anatomical structure is a left ventricle.

21. The computer readable program storage device of claim 20, wherein specifying a plurality of landmark points on said deformable shape comprises:
  identifying a center point of the LV in a short axis view slice of the mid-ventricular region;

specifying an intersecting point of the inferior right ventricle (RV) and the inferior ventricular septum (VS) in the short axis view slice;

connecting the center point and the intersecting point with a first line that separates the inferior VS from the inferior left ventricle free wall (LVFW) and the anterior LVFW from the antero-lateral LVFW;

determining second, third and fourth lines by rotating said first line in 45 degrees increments with respect to the LV center point;

dividing the LVFW and VS into eight segments by the first, second third and fourth lines, wherein each of the first, second third and fourth lines represents a 3D slice along the short axis view;

extracting a slice between an antero-lateral LVFW and a postero-lateral LVFW as a four chamber view;

specifying an LV apex and first and second bottom corner points of an LV wall;

segmenting the LV wall into an apical part, a mid part, and a basal part between said apex and said first and second bottom points, each LV wall part having substantially equal height;

adjusting a 3D pose of the LV wall;

determining the LV pose along a long-axis view;

for each 3D slice along the short axis view, specifying one point at the apex and ten points evenly distributed along an interior surface of the LV wall and VS; and averaging the coordinates of the apex points to determine a final apex location.

22. The computer readable program storage device of claim 21, wherein adjusting a 3D pose of the LV wall comprises:

defining an orientation line connecting the apex point and a center point between the first and second bottom points; and defining first second, third, and fourth segmenting slices along the four chamber view as slices substantially perpendicular to the orientation line with substantially equal distances between the apex and a bottom line connecting the first and second bottom corner points.

23. The computer readable program storage device of claim 21, wherein determining the LV pose along a long-axis view comprises:

extracting a slice between an inferior LVFW and an infero-posterior LVFW as a long axis view; and specifying the LV apex in said long axis view and determining the LV pose along the long-axis view based on the LV apex and the LV center point.

24. The computer readable program storage device of claim 17, wherein the image is a 3D ultrasound image.

25. The computer readable program storage device of claim 17, wherein computing motion parameters includes using estimated motion parameters from a previous iteration.

26. The computer readable program storage device of claim 17, wherein computing motion parameters from said Jacobian matrix and present and reference image values in said cuboid comprises calculating $$\Delta\mu = -\left(\sum_{P\in S} J_P^T J_P\right)^{-1}\left(\sum_{P\in S} I_{tP} J_P^T\right),$$

wherein $\Delta\mu=(\theta_x,\theta_y,\theta_z,t_x,t_y,t_z)$ wherein $\theta_i$ is an infinitesimal rotation in the ith direction, $t_i$ is a translation in the ith direction, $I_{tP}=\hat{I}(\hat{P})-I(P)$ wherein I is the reference image and P is the at least one point in the reference image, $\hat{I}$ is the present image and $\hat{P}$ is the point $\hat{I}$ corresponding to P, $J_P$ is the Jacobian matrix, and S is the cuboid.

* * * * *